(12) United States Patent
Kitano (10) Patent No.: US 10,591,713 B2
(45) Date of Patent: Mar. 17, 2020

(54) ENDOSCOPE HAVING AN IMAGING UNIT (71) Applicant: FUJIFILM Corporation, Tokyo (JP)

(72) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 190 days.

(21) Appl. No.: 15/433,976

(22) Filed: Feb. 15, 2017

(65) Prior Publication Data

US 2017/0248780 A1 Aug. 31, 2017

(30) Foreign Application Priority Data

Feb. 25, 2016 (JP) ................................ 2016-034400

(51) Int. Cl.
*G02B 23/24* (2006.01)
*A61B 1/05* (2006.01)

(52) U.S. Cl.
CPC .......... *G02B 23/2484* (2013.01); *A61B 1/051* (2013.01); *G02B 23/2423* (2013.01); *G02B 23/2446* (2013.01); *G02B 23/2469* (2013.01)

(58) Field of Classification Search
CPC ....... A61B 1/051; A61B 1/053; A61B 1/0669; G02B 23/2476; G02B 23/2484; H04N 2005/2255; H04N 5/2253
USPC ........................................................ 600/110
See application file for complete search history.

(56) References Cited

U.S. PATENT DOCUMENTS

| | | | | |
|---|---|---|---|---|
| 6,313,456 | B1* | 11/2001 | Miyashita | ......... H01L 27/14618 250/208.1 |
| 8,679,000 | B2* | 3/2014 | Kimura | ................... A61B 1/051 600/110 |
| 9,711,912 | B2* | 7/2017 | Xing | ..................... H01R 13/659 |
| 10,039,437 | B2* | 8/2018 | Tanahashi | ................ A61B 1/00 |

(Continued)

FOREIGN PATENT DOCUMENTS

| | | |
|---|---|---|
| CN | 101102714 | 1/2008 |
| EP | 2407084 | 1/2012 |

(Continued)

OTHER PUBLICATIONS

"Search Report of Europe Counterpart Application", dated Jul. 24, 2017, p. 1-p. 7, in which the listed references were cited.

(Continued)

*Primary Examiner* — John P Leubecker
*Assistant Examiner* — Shankar Raj Ghimire
(74) *Attorney, Agent, or Firm* — JCIPRNET (57) ABSTRACT

An endoscope has an imaging unit at a tip portion of an insertion unit to be inserted into a body cavity, the imaging unit includes: a solid-state imaging device which performs photoelectric conversion on an optical image formed on a photodetecting surface thereof; a circuit board having a connection surface which is opposed to a surface, opposite to the photodetecting surface and formed with terminals, of the imaging device and which serves for electrical connection to the terminals; and a case member which covers part of the imaging device and part of the circuit board, the circuit board has a wide portion and a narrow portion that are (Continued)

different in length in a width direction perpendicular to a longitudinal direction of the insertion unit, and the case member is formed with first cuts in such a range as to correspond to the wide portion in the longitudinal direction.

16 Claims, 8 Drawing Sheets (56) References Cited

U.S. PATENT DOCUMENTS

| | | | | |
|---|---|---|---|---|
| 10,070,774 | B2* | 9/2018 | Levi | A61B 1/00089 |
| 2008/0111907 | A1* | 5/2008 | Ito | H04N 5/2253 |
| | | | | 348/311 |
| 2008/0249363 | A1 | 10/2008 | Nakamura et al. | |
| 2011/0092769 | A1* | 4/2011 | Kokubo | A61B 1/05 |
| | | | | 600/109 |
| 2011/0211053 | A1* | 9/2011 | Nakayama | A61B 1/051 |
| | | | | 348/76 |
| 2011/0249106 | A1* | 10/2011 | Makino | H04N 5/2254 |
| | | | | 348/76 |
| 2012/0197081 | A1* | 8/2012 | Kimura | A61B 1/00124 |
| | | | | 600/110 |
| 2013/0035546 | A1* | 2/2013 | Lin | A61B 1/0011 |
| | | | | 600/109 |
| 2014/0316198 | A1* | 10/2014 | Krivopisk | A61B 1/00181 |
| | | | | 600/109 |
| 2014/0320621 | A1* | 10/2014 | Sonnenschein | A61B 1/00096 |
| | | | | 348/76 |
| 2014/0362286 | A1* | 12/2014 | Komi | G06K 7/10732 |
| | | | | 348/374 |
| 2015/0228678 | A1* | 8/2015 | Yoshida | A61B 1/00071 |
| | | | | 600/110 |
| 2015/0305601 | A1* | 10/2015 | Levi | A61B 1/00089 |
| | | | | 600/104 |
| 2017/0086660 | A1* | 3/2017 | Igarashi | H05K 3/32 |
| 2017/0224203 | A1* | 8/2017 | Tanahashi | A61B 1/04 |
| 2018/0000327 | A1* | 1/2018 | Kojima | A61B 1/04 |

FOREIGN PATENT DOCUMENTS

| | | | |
|---|---|---|---|
| FR | 2737650 | 2/1997 | |
| JP | 2012055489 | 3/2012 | |
| JP | 2012157472 | 8/2012 | |
| JP | 2015-058118 | 3/2015 | |
| WO | 2015194279 | 12/2015 | |
| WO | WO-2015194279 A1 * | 12/2015 | H05K 3/32 |

OTHER PUBLICATIONS

"Notification of Reasons for Refusal of Japan Counterpart Application," dated Dec. 4, 2018, with English translation thereof, p. 1-p. 4.

"Office Action of China Counterpart Application," with English translation thereof, dated Dec. 4, 2019, p. 1-p. 12.

* cited by examiner

ENDOSCOPE HAVING AN IMAGING UNIT

CROSS-REFERENCE TO RELATED APPLICATIONS

This application claims the benefit of Japanese Patent Application JP 2016-034400, filed Feb. 25, 2016, the entire content of which is hereby incorporated by reference, the same as if set forth at length.

FIELD OF THE INVENTION

The present invention relates to an endoscope.

BACKGROUND OF THE INVENTION

In general, an imaging unit that is installed in a tip portion of an insertion unit of an endoscope is equipped with an image sensor and a circuit board on which the image sensor is mounted. And plural electric wires inserted through the insertion unit are connected to the circuit board.

JP-A-2015-58118 discloses an imaging unit which is equipped with a case member (cover member) that covers an image sensor and a circuit board.

SUMMARY OF THE INVENTION

To protect a connection portion of an image sensor and a circuit board and to increase the durability of connection portions of the circuit board and electric wires, it is desirable to cover a region from the image sensor to the connection portions of the circuit board and the electric wires with a case member that is high in stiffness. However, a configuration in which the image sensor and the circuit board are fully covered with the case member has a problem that the image sensor and the circuit board may not be able to be housed in the case member when an error occurs in the position of attachment of the circuit board to the image sensor. Employing a larger case member taking an error in the attachment position of the circuit board into consideration is not preferable because it may cause size increase of the imaging unit and thereby obstruct narrowing of an insertion unit of an endoscope.

The present invention has been made in view of the above circumstances, and an object of the invention is therefore to provide an endoscope in which an image sensor and a circuit board can be housed in a case member even if an error occurs in the position of attachment of the circuit board to the image sensor.

An endoscope according to an aspect of the invention is an endoscope having an imaging unit at a tip portion of an insertion unit to be inserted into a body cavity, the imaging unit comprising: a solid-state imaging device which performs photoelectric conversion on an optical image formed on a photodetecting surface of the solid-state imaging device; a circuit board having a connection surface which is opposed to a surface, opposite to the photodetecting surface and formed with terminals, of the solid-state imaging device and which serves for electrical connection to the terminals of the solid-state imaging device; and a case member which covers part of the solid-state imaging device and part of the circuit board, wherein: the circuit board has a wide portion and a narrow portion that are different from each other in the length in a width direction that is perpendicular to the longitudinal direction of the insertion unit; and the case member is formed with first cuts in such a range as to correspond to the wide portion of the circuit board in the longitudinal direction of the insertion unit.

In the invention, the circuit board has the wide portion and the narrow portion and the case member is formed with the first cuts in such a range as to correspond to the wide portion of the circuit board in the longitudinal direction of the insertion unit. By virtue of this structure, even if an error occurs in the position of attachment of the circuit board to the image sensor, the image sensor and the circuit board can be housed in the case member. Thus, it is not necessary to set the size of the case member larger taking an error in the attachment position of the circuit board into consideration. As a result, the insertion unit of the endoscope can be narrowed and the durability of the imaging unit can be increased by the case member.

DESCRIPTION OF SYMBOLS

1: Endoscope system
2: Endoscope
20: Imaging unit
21: Image sensor
21a: Photodetecting surface
22: Lens barrel (imaging optical system)
23: Sensor holder
24: Circuit board
24A: Wide portion
24B: Narrow portion
26: Terminal
27: Electric wire
28: Case member
30: Sensor connection portion
30a: Connection surface
31: Electric wire connection portion
33: Holding portion
34: Cover portion
51: First cut
52: Second cut

DETAILED DESCRIPTION OF THE INVENTION

Figure 1:
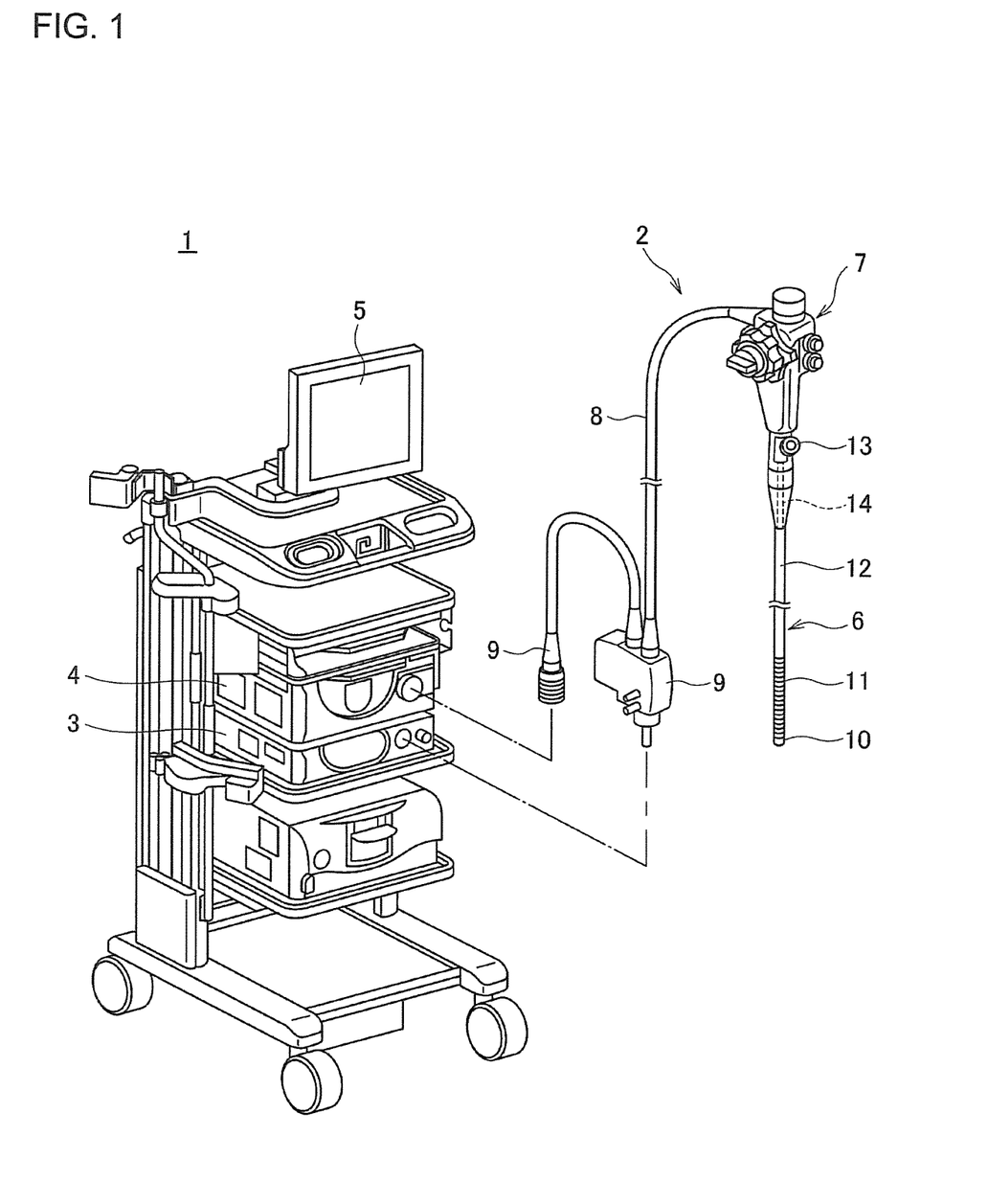
FIG. 1 shows the configuration of an example endoscope system for description of an embodiment of the present invention.
Figure 2:
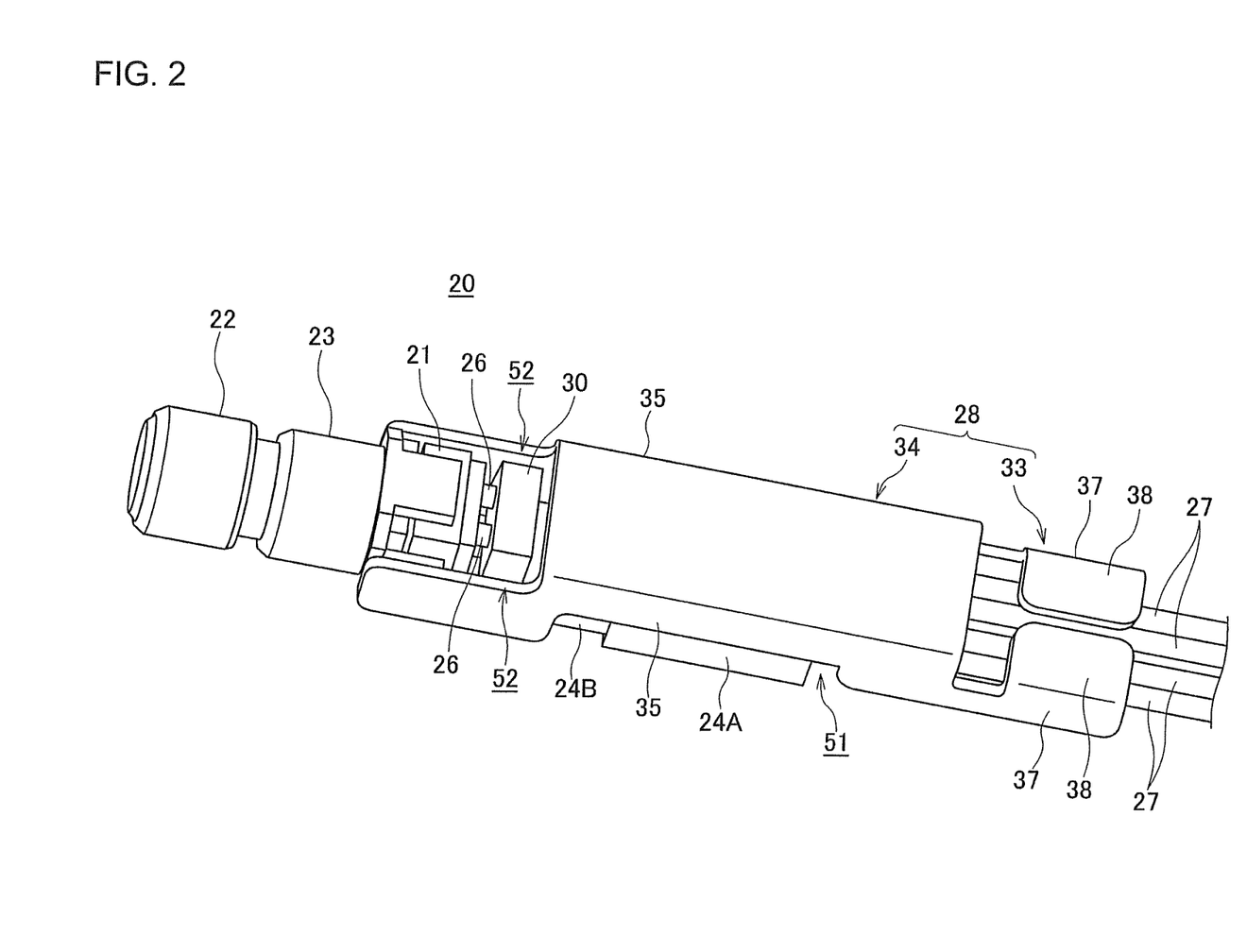
FIG. 2 is a perspective view of an imaging unit that is installed in a tip portion of an insertion unit of an endoscope shown in FIG. 1.
Figure 3:
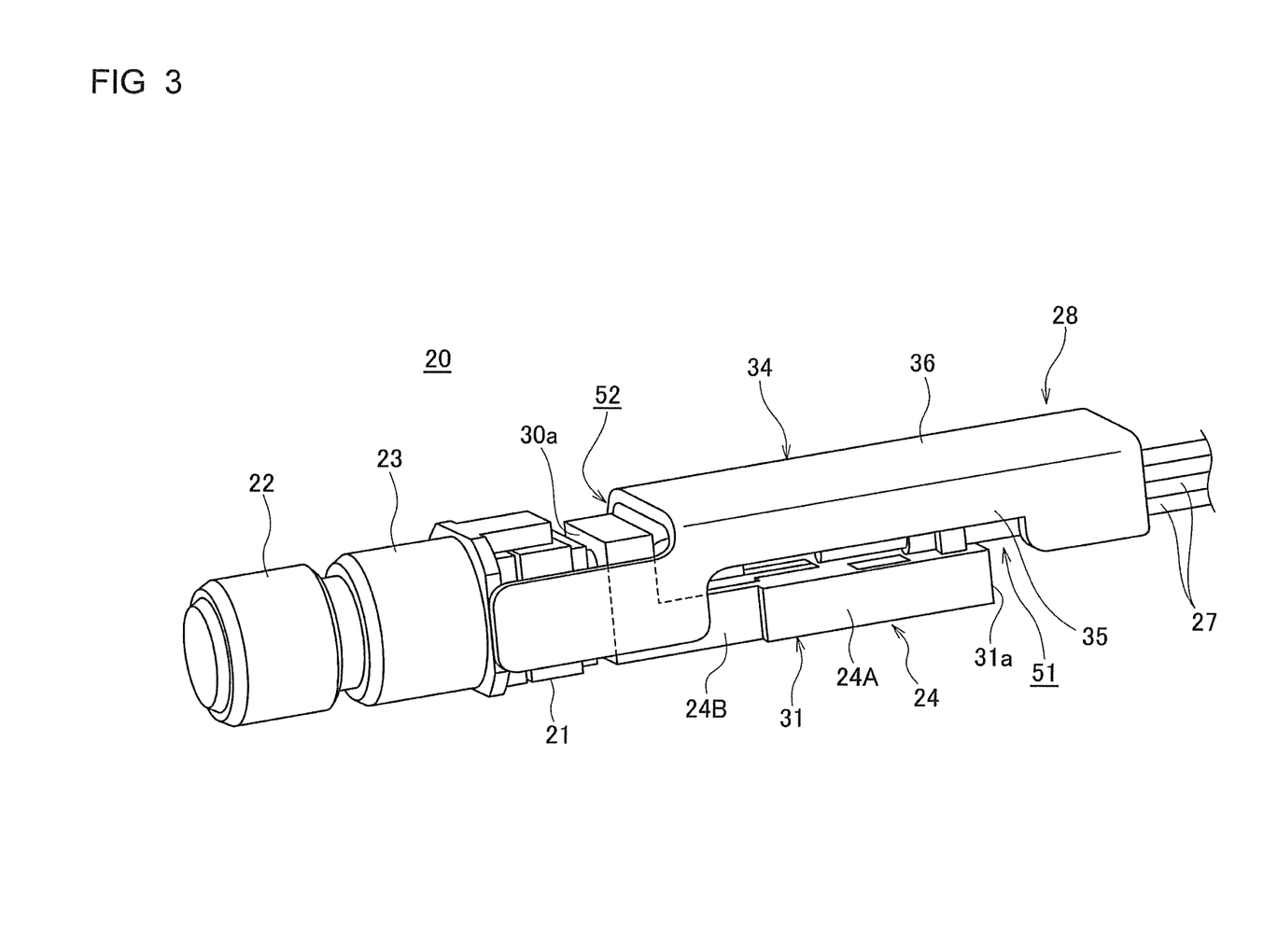
FIG. 3 is a perspective view, as viewed from a different direction than in FIG. 2, of the imaging unit installed in the tip portion of the insertion unit of the endoscope shown in FIG. 1.

FIG. 1 shows an example endoscope system 1 for description of an embodiment of the present invention. The endoscope system 1 is composed of an endoscope 2, a light source unit 3, and a processor unit 4. The endoscope 2 is equipped with an insertion unit 6 to be inserted into a subject body, a manipulation unit 7 which is continuous with the insertion unit 6, and a universal cord 8 which extends from the manipulation unit 7. The insertion unit 6 is composed of a tip portion 10, a bendable portion 11 which is continuous with the tip portion 10, and a soft portion 12 which links the bendable portion 11 to the manipulation unit 7.

The tip portion 10 is equipped with illumination optical systems for emitting illumination light for illumination of an observation part, an imaging unit and an imaging optical system for shooting the observation part, and other components. The bendable portion 11 is configured so as to be bendable perpendicularly to the longitudinal axis of the insertion unit 6, and is bent by manipulating the manipulation unit 7. The soft portion 12 is configured so as to be relatively flexible, that is, flexible enough to deform so as to conform to the shape of an insertion route for the insertion unit 6.

The manipulation unit 7 is equipped with buttons for making a manipulation for an imaging operation of the imaging unit installed in the tip portion 10, a knob for making a manipulation for bending the bendable portion 11, and other members. The manipulation unit 7 is formed with an insertion inlet 13 through which a treatment tool such as an electric scalpel is to be inserted, and a treatment tool channel 14 through which a treatment tool is to be inserted is formed in the insertion unit 6 so as to extend from the insertion inlet 13 to the tip portion 10.

Connectors 9 are provided at an intermediate position and one end of the universal cord 8. The endoscope 2 is connected, via the connector(s) 9, to the light source unit 3 for generating illumination light to be emitted from the illumination optical system provided in the tip portion 10 and the processor unit 4 for processing a video signal acquired by the imaging unit provided in the tip portion 10. The processor unit 4 generates video data of an observation part by processing a received video signal and displays the generated video data on a monitor 5. Furthermore, the processor unit 4 has the generated video data recorded.

Light guides and electric wires are disposed inside the insertion unit 6, the manipulation unit 7, and the universal cord 8. Illumination light generated by the light source unit 3 is guided by the light guides to the illumination optical systems provided in the tip portion 10, and signals and power are transmitted between the image unit provided in the tip portion 10 and the processor unit 4 by the electric wires.

FIGS. 2 to 6 show the configuration of the imaging unit 20 installed in the tip portion 10 of the insertion unit 6. The imaging unit 20 is equipped with an image sensor (solid-state imaging device) 21 such as a CCD (charge-coupled device) image sensor or a CMOS (complementary metal-oxide-semiconductor) image sensor, a lens barrel 22 which houses an imaging optical system for forming a subject image on a photodetecting surface 21a of the image sensor 21, a sensor holder 23 which holds the image sensor 21 and the lens barrel 22, a circuit board 24 on which the image sensor 21 is mounted, and a case member 28 which covers part of the image sensor 21 and part of the circuit board 24.

The sensor holder 23 holds the lens barrel 22 in such a manner that the lens barrel 22 is movable along the optical axis B (see FIG. 6) of the imaging optical system and the position of the image sensor 21 is thereby adjustable relative to the imaging optical system. The lens barrel 22 is fixed to the sensor holder 23 with, for example, adhesive after the image sensor 21 is positioned with respect to it.

The image sensor 21 is disposed in such a manner that its photodetecting surface 21a crosses the longitudinal direction of the insertion unit 6, and performs photoelectric conversion on an optical image formed on the photodetecting surface 21a. The outer size of the image sensor 21 is smaller than or equal to a 1-mm square when viewed perpendicularly to the photodetecting surface 21a. The back surface of the image sensor 21, that is, its surface opposite to the photodetecting surface 21a, is provided with plural terminals 26 for receiving and outputting signals and power.

The circuit board 24 has a sensor connection portion 30 and an electric wire connection portion 31. The sensor connection portion 30 has a connection surface 30a which is opposed to the surface, opposite to the photodetecting surface 21a and provided with the terminals 26, of the image sensor 21 and serves for electric connection to the respective terminals 26 of the image sensor 21.

The connection surface 30a of the sensor connection portion 30 is formed with plural lands 25. The sensor connection portion 30 is set adjacent to the back surface of the image sensor 21, and the terminals 26 formed on the back surface of the image sensor 21 are connected to the respective lands 25 of the sensor connection portion 30.

The circuit board 24 is a rigid circuit board that is L-shaped when viewed in the width direction (indicated by arrow W in FIG. 4) that is perpendicular to the longitudinal direction of the insertion unit 6. The sensor connection portion 30 and the electric wire connection portion 31 are approximately perpendicular to each other. More specifically, in the embodiment, one of two legs constituting the circuit board 24 is the sensor connection portion 30 and the other is the electric wire connection portion 31. The sensor connection portion 30 is set adjacent to the back surface of the image sensor 21 and parallel with its photodetecting surface 21a. The electric wire connection portion 31 exists behind the image sensor 21 and extends approximately perpendicularly to its photodetecting surface 21a. Alternatively, the circuit board 24 may be a flexible circuit board.

The sensor connection portion 30 is also formed with plural lands 32, and exposed portions of center conductors in tip portions of terminal portions of plural electric wires 27 arranged in a plane that is parallel with the board surface of the electric wire connection portion 31 are connected to the respective lands 32. The circuit board 24 and the image sensor 21 mounted on it are connected to the processor unit 4 via the plural electric wires 27. The plural electric wires 27 are transmission cables.

The circuit board 24 has a wide portion 24A and a narrow portion 24B which are different from each other in the length in the width direction W. The wide portion 24A extends from an end 31a, on the side where the electric wires 27 are connected, of the electric wire connection portion 31 to a position near the sensor connection portion 30. The narrow portion 24B is the portion of the circuit board 24 other than the wide portion 24A, and hence the sensor connection portion 30 belongs to the narrow portion 24B.

The case member 28 has a holding portion 33 which hold the plural electric wires 27 and a cover portion 34 which covers part of the image sensor 21 and part of the circuit board 24. The cover portion 34 is composed of a pair of side walls 35 and a ceiling wall 36 which connects the pair of side walls 35.

The pair of side walls 35 extend alongside a pair of side surfaces, extending perpendicularly to the photodetecting surface 21a of the image sensor 21, of the circuit board 24, respectively. Each of the pair of side walls 35 is formed with a first cut 51 in such a range as to correspond to the wide portion 24A of the circuit board 24 in the longitudinal direction of the insertion unit 6 so as not to interfere with the wide portion 24A in the width direction W. Part of the narrow portion 24B of the circuit board 24 is interposed between portions, extending to beside the image sensor 21, of the pair of side walls 35 in the width direction W with gaps D (see FIG. 4). Image-sensor-21-side tip portions of the pair of side walls 35 are fixed to the sensor holder 23 with adhesive, for example.

The ceiling wall 36 covers the board surface, formed with the lands 32, of the electric wire connection portion 31 of the circuit board 24 and the terminal portions, connected to the respective lands 32, of the electric wires 27. The ceiling wall 36 is formed with a second cut 52 above the leg, having the connection surface 30a, of the circuit board 24, that is, the sensor connection portion 30. The second cut 52 extends to over the image sensor 21 from a position, close to the sensor connection portion 30, of the ceiling wall 36.

The holding portion 33 has a pair of extension side walls 37 that are connected to the pair of side walls 35 of the cover portion 34, respectively. The pair of extension side walls 37 project rearward from the cover portion 34 perpendicularly to the photodetecting surface 21a of the image sensor 21 and are located on the two respective sides, in the arrangement direction of the plural electric wires 27, of the electric wires 27 which are arranged in a plane that is parallel with the board surface of the electric wire connection portion 31 of the circuit board 24.

Presser pieces 38 project from the top edges of the pair of extension side walls 37, respectively, and are placed on the plural electric wires 27 interposed between the pair of extension side walls 37 from the side opposite to the board surface of the electric wire connection portion 31. As a result, the plural electric wires 27 are kept arranged in the same plane even in the rear of the electric wire connection portion 31 as over the board surface of the electric wire connection portion 31.

The presser pieces 38 which are placed on the plural electric wires 27 are located closer to the side of the electric wire connection portion 31 than the ceiling wall 36 of the cover portion 34 is, and a step is thereby formed between the ceiling wall 36 and the presser pieces 38.

Figure 7:
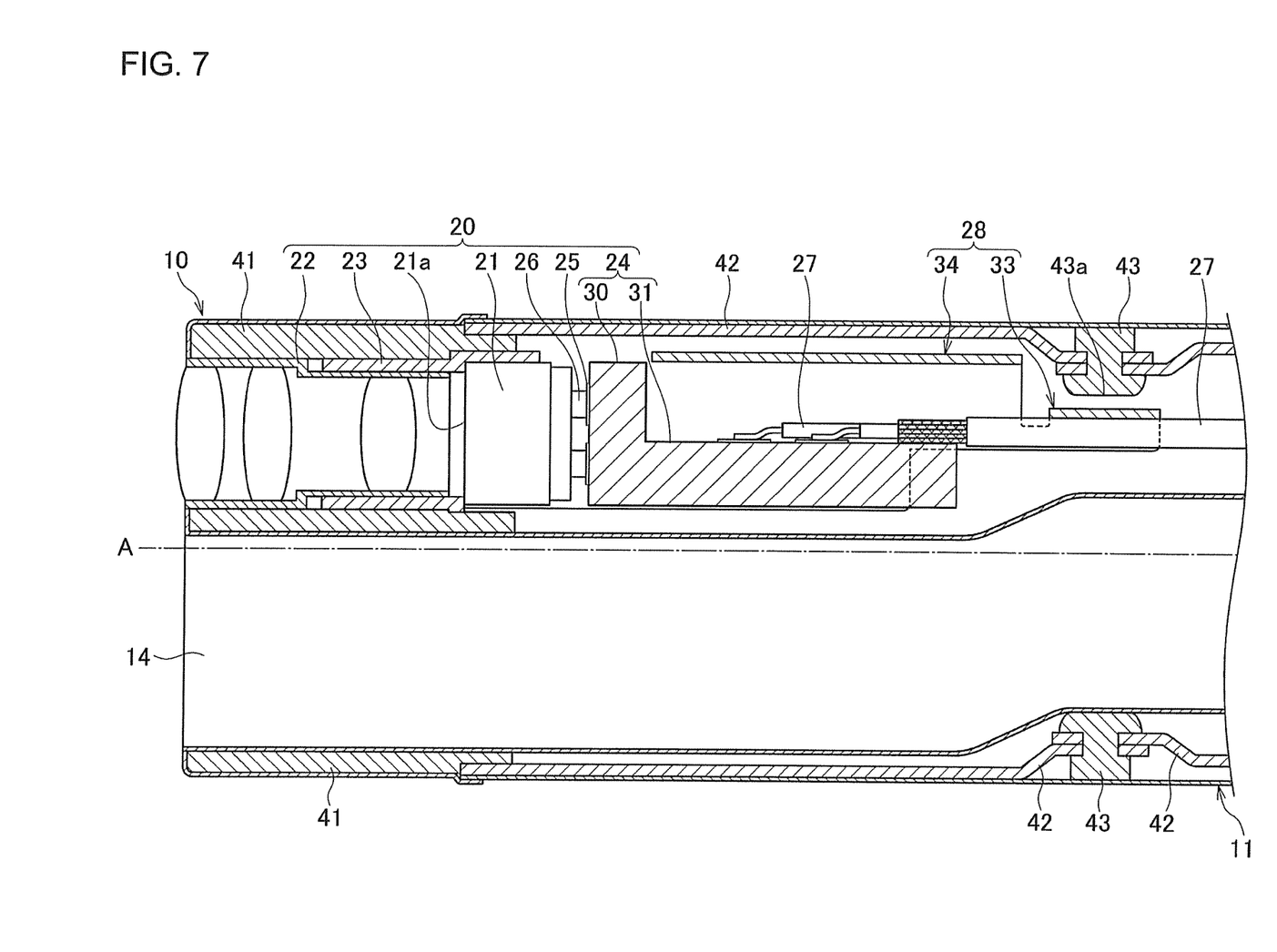
FIG. 7 is a longitudinal sectional view of the tip portion and a bendable portion of the insertion unit of the endoscope shown in FIG. 1.
Figure 8:
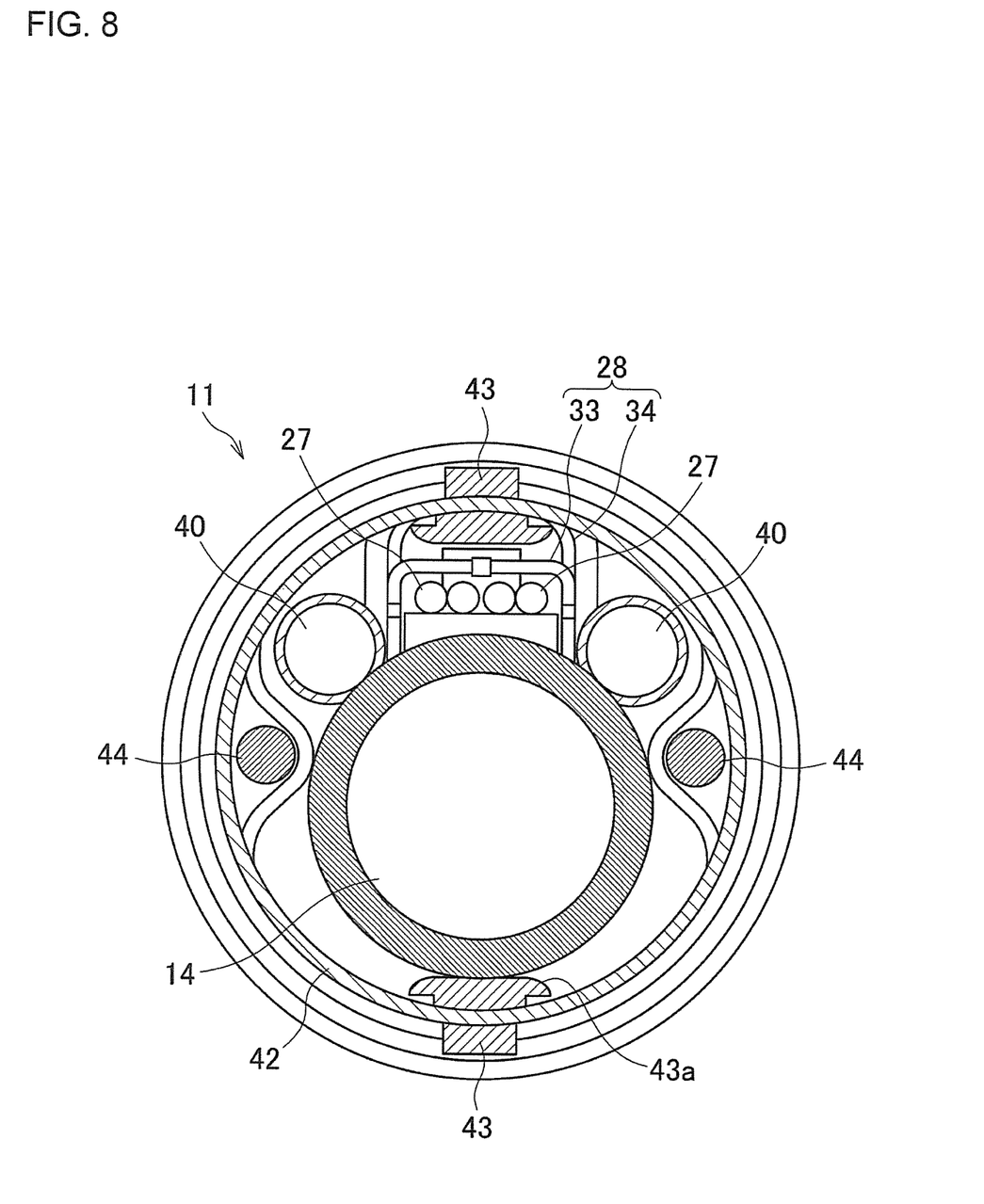
FIG. 8 is a transverse sectional view of the bendable portion of the insertion unit of the endoscope shown in FIG. 1.

FIGS. 7 and 8 illustrate the structures of the tip portion 10 in which the imaging unit 20 is installed and the bendable portion 11 of the insertion unit 6.

The above-described imaging unit 20, a tip portion of the treatment tool channel 14, the illumination optical systems for emitting illumination light guided from the light source unit 3 by the light guides 40, and other members are disposed in the tip portion 10.

The sensor holder 23 which holds the image sensor 21 and the lens barrel 22 is disposed in a housing hole of a tip hard portion 41 which is made of a metal material such as stainless steel, and is fixed to the tip hard portion 41. The tip portion of the treatment tool channel 14 and the illumination optical systems are also disposed in the housing hole of the tip hard portion 41 and are fixed to the tip hard portion 41.

The photodetecting surface 21a of the image sensor 21 which is held by the sensor holder 23 fixed to the tip hard portion 41 is oriented approximately perpendicularly to the longitudinal axis A of the insertion unit 6. The electric wire connection portion 31 which is approximately perpendicular to the photodetecting surface 21a extends parallel with the longitudinal axis A.

The bendable portion 11 includes plural ring-shaped joining pieces 42 which are arranged parallel with the longitudinal axis A, and is thereby formed as a tubular body that houses the plural electric wires 27 connected to the circuit board 24 of the imaging unit 20, the treatment tool channel 14, the light guides 40, etc.

Two adjoining joining pieces 42 are connected to each other by a pair of pins 43 disposed on an axial line that is approximately perpendicular to the longitudinal axis A, so as to be swingable about the axial line. The bendable portion 11 is bent as a whole as a result of combination of individual swings of pairs of adjoining joining pieces 42.

The bendable portion 11 is manipulated by the manipulation unit 7 via a pair of wires 44 which are inserted through the bendable portion 11 past the soft portion 12. When manipulated by the manipulation unit 7, one of the pair of wires 44 is pulled and the other is paid out, whereby the bendable portion 11 is bent.

Among the plural joining pieces 42 constituting the bendable portion 11, the head joining piece 42 located in the tip portion 10 is joined to the tip hard portion 41, whereby the tip portion 10 and the bendable portion 11 are connected to each other. In the tip portion 10 of the insertion unit 6, the circuit board 24 and the case member 28 of the imaging unit 20 whose sensor holder 23 is fixed to the tip hard portion 41 are disposed inside the head joining piece 42.

Heads 43a of the pair of pins 43 that connect the head joining piece 42 and the joining piece 42 adjacent to it project inward in the radial direction. A narrower space is formed at the position of this pair of pins 43 so as to be perpendicular to the axial direction of the insertion unit 6 and to be narrower in the radial direction than the portions, distant from the pair of pins 43 in the axial direction, of the two joining pieces 42 connected by the pair of pins 43.

The holding portion 33 of the case member 28 which is disposed inside the head joining piece 42 is located between the pair of pins 43, that is, in the narrower space formed inside the insertion unit 6, and holds, between the pair of pins 43, the plural electric wires 27 which are connected to the electric wire connection portion 31 of the circuit board 24.

As described above, in the embodiment, the circuit board 24 has the wide portion 24A and the narrow portion 24B which are different from each other in length in the width direction (indicated by arrow W in FIG. 4) which is perpendicular to the longitudinal direction of the insertion unit 6. And each of the pair of side walls 35 of the cover portion 34 and the case member 28 is formed with the first cut 51 in such a range as to correspond to the wide portion 24A of the circuit board 24 in the longitudinal direction of the insertion unit 6. By virtue of this structure, even if an error occurs, in the direction W, in the position of attachment of the circuit board 24 to the image sensor 21, the image sensor 21 and the circuit board 24 can be housed in the case member 28 with no interference between the wide portion 24A of the circuit board 24 and the case member 28.

The ceiling wall 36 of the case member 28 is formed with the second cut 52 which extends to over the image sensor 21 from a position, close to the sensor connection portion 30, of the ceiling wall 36. By virtue of this structure, even if an error occurs, in the direction that is perpendicular to the direction W and toward the ceiling wall 36, in the position of attachment of the circuit board 24 to the image sensor 21, the image sensor 21 and the circuit board 24 can be housed in the case member 28 with no interference between the circuit board 24 and the case member 28. Thus, it is not necessary to set the size of the case member 28 larger taking an error in the attachment position of the circuit board 24 into consideration. As a result, the insertion unit 6 of the endoscope 2 can be narrowed and the durability of the imaging unit 20 can be increased by the case member 28.

In particular, in the embodiment, although the outer size of the image sensor 21 is smaller than or equal to a 1-mm square and hence the imaging unit 20 is required to be very high in dimensional accuracy, the imaging unit 20 can be miniaturized with high accuracy because as described above the circuit board 24 and the case member 28 do not interfere with each other.

Since the plural electric wires 27 are connected to the wide portion 24A of the circuit board 24, it is not necessary to reduce the area of the lands 32 which are portions for electrical connection between the circuit board 24 and the electric wires 27. Thus, reduction in the strength of connection between the plural electric wires 27 and the circuit board 24 is not incurred.

Figure 4:
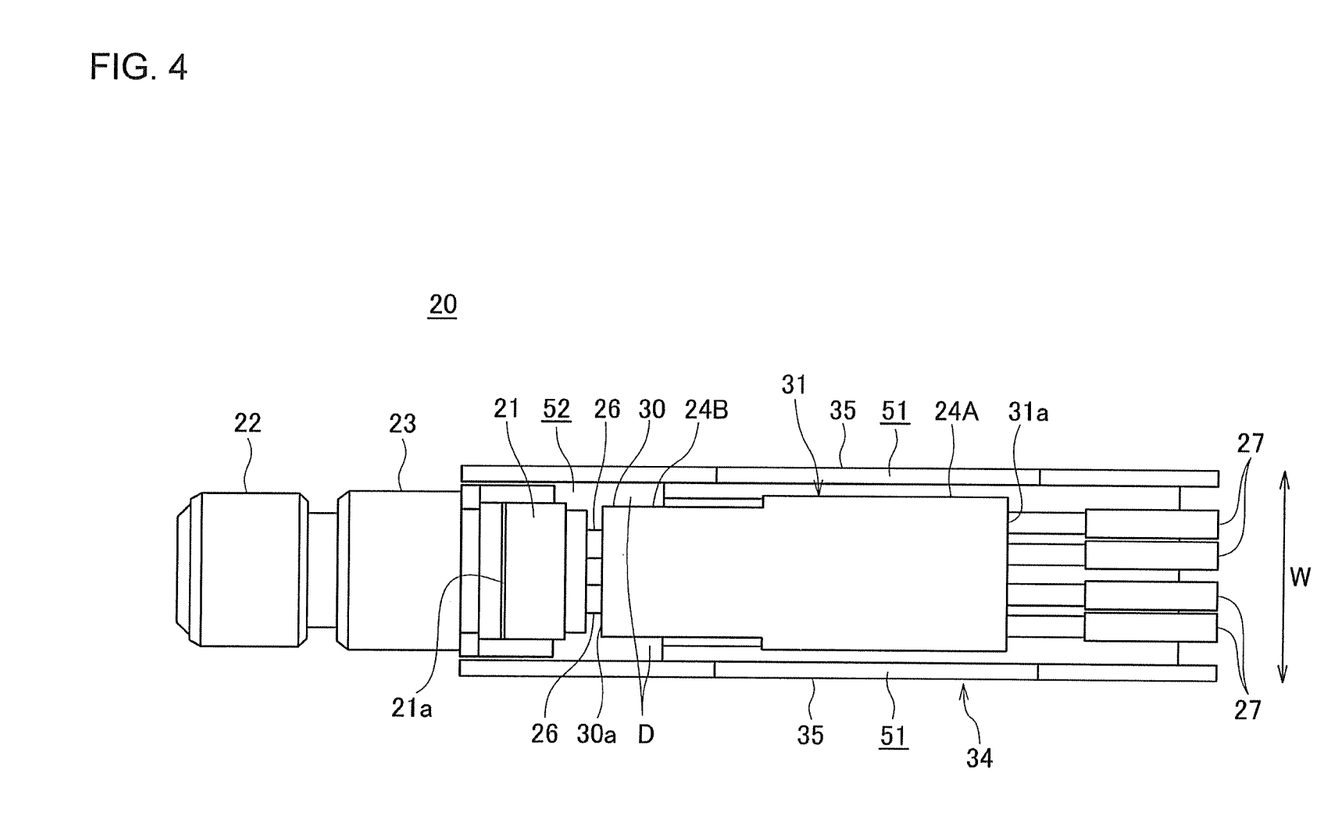
FIG. 4 is a bottom view of the imaging unit shown in FIG. 2.
Figure 5:
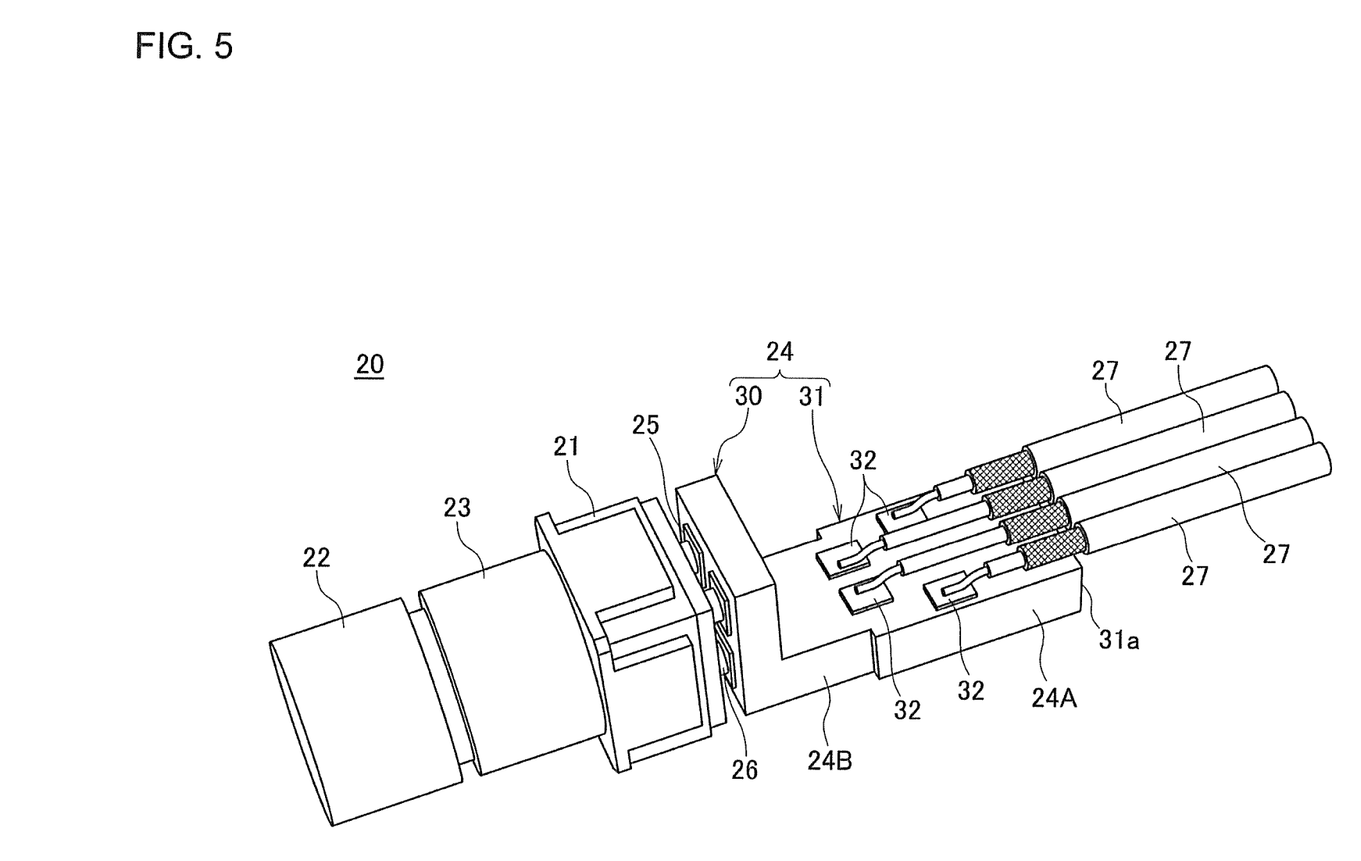
FIG. 5 is a perspective view showing the inside of the imaging unit shown in FIG. 2.
Figure 6:
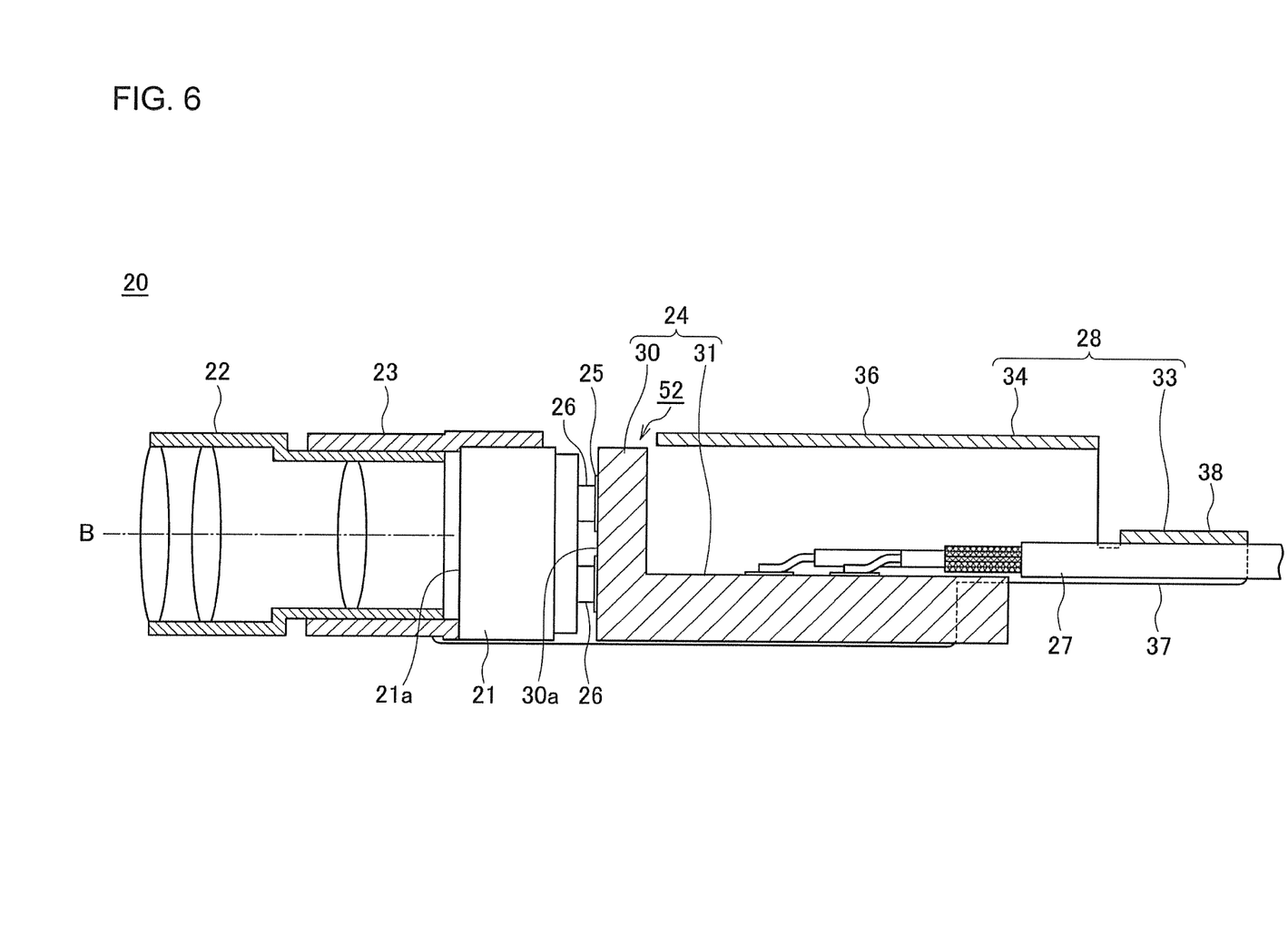
FIG. 6 is a sectional view of the imaging unit of FIG. 2.

Part of the narrow portion 24B of the circuit board 24 is interposed between the pair of side walls 35 of the case member 28 with gaps D (see FIG. 4). Thus, even if an error as large as the gap D occurs in the direction W in attaching the circuit board 24 to the image sensor 21, the error is allowable because of the presence of the gaps D.

Although in the embodiment the circuit board 24 is L-shaped, it may have other shapes such as a flat-plate shape.

As described above, an endoscope described herein is an endoscope having an imaging unit in a tip portion of an insertion unit to be inserted into a body cavity, the imaging unit comprising: a solid-state imaging device which performs photoelectric conversion on an optical image formed on a photodetecting surface of the solid-state imaging device; a circuit board having a connection surface which is opposed to a surface, opposite to the photodetecting surface and formed with terminals, of the solid-state imaging device and which serves for electrical connection to the terminals of the solid-state imaging device; and a case member which covers part of the solid-state imaging device and part of the circuit board, wherein: the circuit board has a wide portion and a narrow portion that are different from each other in the length in a width direction that is perpendicular to the longitudinal direction of the insertion unit; and the case member is formed with first cuts in such a range as to correspond to the wide portion of the circuit board in the longitudinal direction of the insertion unit.

Further, transmission cables may be electrically connected to the wide portion of the circuit board.

Further, the solid-state imaging device may be disposed in such a manner that its photodetecting surface crosses the longitudinal direction of the insertion unit; the circuit board may be L-shaped when viewed in the width direction; the connection surface may be a surface of one of two legs constituting the circuit board; and the case member may be formed with a second cut adjacent to an end portion of the leg having the connection surface.

Further, at least part of the narrow portion of the circuit board may be interposed between portions of the case member in the width direction with gaps.

Further, an outer size of the solid-state imaging device may be smaller than or equal to a 1-mm square when viewed perpendicularly to its photodetecting surface.

What is claimed is:

1. An endoscope having an imaging unit at a tip portion of an insertion unit to be inserted into a body cavity, the imaging unit comprising:
   a solid-state imaging device which performs photoelectric conversion on an optical image formed on a photodetecting surface of the solid-state imaging device;
   a circuit board having a connection surface which faces a surface of the solid-state imaging device, the surface being opposite to the photodetecting surface and being formed with terminals, the connection surface serving for electrical connection to the terminals of the solid-state imaging device; and
   a case member which covers part of the solid-state imaging device and part of the circuit board, wherein:
   the circuit board has a wide portion and a narrow portion that are different from each other in length in a width direction that is perpendicular to a longitudinal direction of the insertion unit, the narrow portion being located between the wide portion and the solid-state imaging device; and
   the case member is formed with first cuts in such a range as to correspond to the wide portion of the circuit board in the longitudinal direction of the insertion unit.

2. The endoscope according to claim 1, wherein transmission cables are electrically connected to the wide portion of the circuit board.

3. The endoscope according to claim 2, wherein:
   the solid-state imaging device is disposed in such a manner that the photodetecting surface crosses the longitudinal direction of the insertion unit;
   the circuit board is L-shaped when viewed in the width direction;
   the connection surface is a surface of one of two legs constituting the circuit board; and
   the case member is formed with a second cut adjacent to an end portion of the leg having the connection surface.

4. The endoscope according to claim 3, wherein at least part of the narrow portion of the circuit board is interposed between portions of the case member in the width direction with gaps.

5. The endoscope according to claim 4, wherein an outer size of the solid-state imaging device is smaller than or equal to a 1-mm square when viewed perpendicularly to the photodetecting surface.

6. The endoscope according to claim 3, wherein an outer size of the solid-state imaging device is smaller than or equal to a 1-mm square when viewed perpendicularly to the photodetecting surface.

7. The endoscope according to claim 2, wherein at least part of the narrow portion of the circuit board is interposed between portions of the case member in the width direction with gaps.

8. The endoscope according to claim 7, wherein an outer size of the solid-state imaging device is smaller than or equal to a 1-mm square when viewed perpendicularly to the photodetecting surface.

9. The endoscope according to claim 2, wherein an outer size of the solid-state imaging device is smaller than or equal to a 1-mm square when viewed perpendicularly to the photodetecting surface.

10. The endoscope according to claim 1, wherein:
    the solid-state imaging device is disposed in such a manner that the photodetecting surface crosses the longitudinal direction of the insertion unit;
    the circuit board is L-shaped when viewed in the width direction;
    the connection surface is a surface of one of two legs constituting the circuit board; and
    the case member is formed with a second cut adjacent to an end portion of the leg having the connection surface.

11. The endoscope according to claim 10, wherein at least part of the narrow portion of the circuit board is interposed between portions of the case member in the width direction with gaps.

12. The endoscope according to claim 11, wherein an outer size of the solid-state imaging device is smaller than or equal to a 1-mm square when viewed perpendicularly to the photodetecting surface.

13. The endoscope according to claim 10, wherein an outer size of the solid-state imaging device is smaller than or equal to a 1-mm square when viewed perpendicularly to the photodetecting surface.

14. The endoscope according to claim 1, wherein at least part of the narrow portion of the circuit board is interposed between portions of the case member in the width direction with gaps.

15. The endoscope according to claim 14, wherein an outer size of the solid-state imaging device is smaller than or equal to a 1-mm square when viewed perpendicularly to the photodetecting surface.

16. The endoscope according to claim 1, wherein an outer size of the solid-state imaging device is smaller than or equal to a 1-mm square when viewed perpendicularly to the photodetecting surface.

\* \* \* \* \*